(12) United States Patent
Cooper

(10) Patent No.: US 8,530,451 B2
(45) Date of Patent: Sep. 10, 2013

(54) METHOD AND COMPOSITION FOR THE CONTROL OF ECTOPARASITES

(75) Inventor: Nigel Cooper, Huddersfield (GB)

(73) Assignee: Thornton & Ross Limited, Huddersfield (GB)

( * ) Notice: Subject to any disclaimer, the term of this patent is extended or adjusted under 35 U.S.C. 154(b) by 0 days.

(21) Appl. No.: 13/266,230

(22) PCT Filed: May 12, 2010

(86) PCT No.: PCT/GB2010/000933
§ 371 (c)(1),
(2), (4) Date: Nov. 28, 2011

(87) PCT Pub. No.: WO2010/130983
PCT Pub. Date: Nov. 18, 2010

(65) Prior Publication Data
US 2012/0071444 A1   Mar. 22, 2012

(30) Foreign Application Priority Data

May 14, 2009 (GB) .................................. 0908226.4
Jul. 14, 2009 (GB) .................................. 0912209.4

(51) Int. Cl.
*A01N 55/00* (2006.01)
*A61K 31/045* (2006.01)
*A61K 31/80* (2006.01)
*A61K 33/00* (2006.01)

(52) U.S. Cl.
USPC ........................................................ 514/63

(58) Field of Classification Search
USPC ........................................................ 514/63
See application file for complete search history.

(56) References Cited

FOREIGN PATENT DOCUMENTS

| | | | |
|---|---|---|---|
| FR | 2823101 | A1 | 10/2002 |
| GB | 1604853 | A | 12/1981 |
| WO | 0119190 | A1 | 3/2001 |
| WO | WO 01/19190 | * | 3/2001 |
| WO | WO 01/19190 | A1 * | 3/2001 |
| WO | 02074088 | A1 | 9/2002 |
| WO | 2007104345 | A2 | 9/2007 |
| WO | 2010018360 | A1 | 2/2010 |

OTHER PUBLICATIONS

Yasufuku, "A flash point behavior of dimethyl silicone liquids," IEEE Transactions on Electrical Insulation, E1-17(4):338-344, 1983.*
Dow Corning document by Cola, Silicone: Preparation, Properties, and Performance. Down Corning Life Sciences. 1-15. 2005.*
Search Report for corresponding WIPO Publication PCT/GB2010/000933.
Priestley C M et al., "Lethality of essential oil constituents towards the human louse, Pediculus humanus, and its eggs", Fitoterapia, IDB Holding, Milan, IT Lnkd-doi: 10.1016/J.Fitote.2006.04.005, vol. 77, No. 4, Jun. 1, 2006 pp. 303-309, XP024925930 ISSN: 0367-326X.
"DOW Cornering 1503 Fluid (Version 1.2)", Internet Citation Jan. 25, 2006, pp. 1-7, XP007914931, www.dowcornering.com/applications/search/products.
"Dow Cornering 556 Cosmetic Grade Fluid (Version 2.2)", Internet Citation Sep. 9, 2010, pp. 1-8, XP007914932, www.dowcornering.com/applications/search/products.
Shin Etsu: "Shin Etsu Shin Etsu Silicone. Silicone Products for Personal Care" Oct. 1, 2008, pp. 1-12, XP007914851, www.in-cosmeticasia.com/ExhibitorLibrary/113/pc_e_1.pdf.
Burgess Ian F: "The mode of action of dimeticone 4% lotion against head lice, Pediculus capitis" BMC Pharmacology, Biomed Central, london, GB LNKD-DOI: 10.1186/1471-2210-9-3, vol. 9, No. 1, Feb. 20, 2009, p. 3, XP021048373 ISSN: 1471-2210.

* cited by examiner

*Primary Examiner* — Jeffrey S. Lundgren
*Assistant Examiner* — Zenab Olabowale
(74) *Attorney, Agent, or Firm* — Egbert Law Offices, PLLC

(57) ABSTRACT

An ectoparasiticidal composition is provided that comprises a mixture of a carrier and an active with an emulsifying agent. The carrier comprises non-volatile low viscosity siloxane and the active comprises a non-volatile high viscosity siloxane. The low viscosity siloxane and the high viscosity siloxane both have a closed cup flash point of at least 100° C. Preferably, both the low viscosity siloxane and the high viscosity siloxane comprise a dimeticone or a dimeticonol or a mixture of same, the the low viscosity siloxane having a viscosity in the range of 5 to 1000 centistokes inclusive and the high viscosity siloxane having a viscosity of at least 1000 centistokes.

24 Claims, 2 Drawing Sheets

METHOD AND COMPOSITION FOR THE CONTROL OF ECTOPARASITES

The present invention relates to ectoparasiticidal compositions and to a method of controlling ectoparasites, in particular head lice and their ova.

Compositions for the control of ectoparasites, in particular head lice, have traditionally comprised conventional insecticides. However, many of these substances have an unpleasant odour and may cause allergic reactions. More recently non-toxic products have been found that are clinically effective. In particular, some silicone polymers, which are widely used in personal care products such as in shampoo and hair conditioners, have been found to be highly effective in eradicating both head lice and their ova when used in certain formulations.

U.S. Pat. No. 4,146,619 describes the use of linear alkyl or aryl siloxane polymers having a viscosity of less than about 20,000 centistokes for use as a pediculicide and/or ovicide. Such polymers are safe to use. However, it has subsequently been found that compositions comprising siloxane polymers with viscosities in excess of 20,000 centistokes are more clinically effective.

U.S. Pat. No. 6,683,065 describes a composition for use as a pediculicide consisting of at least about 40% of polydimethylsiloxane wherein the surface tension of the composition is below about 25 dynes/centimeter at 20° C. and the viscosity of the composition is above about 200 centistokes at 20° C. This composition uses the efficacy of dimeticones, but the high viscosity specified does not allow penetration of the composition through and across the surfaces of the hair. In addition, such high viscosity siloxanes have been found difficult wash out of the hair satisfactorily after use. This makes them difficult and unpleasant to use.

In contrast, EP1215965 describes the use of a composition comprising as active ingredient at least one siloxane derivative, other than solely a linear alkyl or aryl siloxane having a viscosity less than 20,000 centistokes, for the control of ectoparasites and, in particular, pediculous infestations. In particular, this patent describes the use of compositions for the control of head lice that comprise a mixture of a volatile siloxane, such as a cyclomethicone, and a non-volatile siloxane, such a dimeticone. In use, when the composition is applied to the hair, the volatile siloxane acts to spread the non-volatile siloxane over the scalp and hair and then evaporates leaving the non-volatile siloxane as an active deposit coating the hair and any lice and ova that are present. One disadvantage of this product is that it has a limited efficacy against head lice ova. However, the major disadvantage of this composition and of other ectoparasiticidal compositions containing volatile siloxanes, such as cyclomethicone, is that they are flammable or combustible and therefore a fire risk.

It will be appreciated that there is no absolute definition of the term "volatile" but in a scientific context it is taken as a measure of the tendency of a substance to vaporize. Most often the term is used to describe a liquid's tendency to evaporate. One way of quantifying this is to determine a liquids heat of vaporization, which is the energy requires to vaporize a given mass of the liquid at a particular temperature. At 25° C., the heat of vaporization of water is 2257 kJ/kg whereas that of ethanol is 840 kJ/kg. In contrast, the heat of vaporization of cyclomethicones is in the region of 157 kJ/kg, which makes them highly volatile to the extent that they exhibit no cooling effect on the skin. It will be appreciated that generally speaking the lower the heat of vaporization, the lower the flash point.

It will be understood that viscosity can be expressed as absolute viscosity, which is measured in poises or centipoises, or as kinematic viscosity. Kinematic viscosity is the ratio of absolute viscosity to density and is measured in stokes or centistokes. For convenience herein viscosity will be expressed in centistokes unless otherwise stated. Where the density of a substance is close to 1, which is the case with dimethicones that typically have specific gravities between 0.96 and 0.98, absolute and kinematic viscosity have almost the same numerical value.

WO 2007104345 also describes a composition for combating ectoparasites, in particular head lice and their ova, the aim of which is to avoid the use of cyclic siloxanes that it considers potentially noxious. The composition described comprises a mixture of a low viscosity linear polysiloxane having a viscosity of less than 10 centistokes, a higher viscosity linear polysiloxane having a viscosity in excess of 90 centistokes, and at least one spreading agent. In particular, the low viscosity polysiloxane is preferably dimethicone having a viscosity of 1 centistoke and the higher viscosity polysiloxane is preferably dimethicone having a viscosity of 100 centistokes. Dimethicones with a viscosity of around 1 centistoke have a flash point of the order of 57° C. and are volatile and therefore combustible. It will therefore be appreciated that in its preferred embodiment this composition is also flammable or combustible.

In view of the foregoing, it will be appreciated that it is most important when using flammable or combustible products for the recipient being treated to keep away from naked flames, lighted cigarettes and the like. Customers may, therefore, be concerned about using such products on children.

Other commercially available pediculicidal products also suffer from the same disadvantages as described above. Some comprise blends of alcohols with siloxanes and are flammable or combustible whereas others use dimeticones that do not spread well and are hard to rinse out after use. It will be appreciated that generally a compromise has to be reached; either the composition comprises non-volatile siloxanes and is hard to rinse out or it comprises a high proportion of volatile siloxanes making the overall composition flammable or combustible and therefore hazardous.

It is an object of the present invention is to provide an ectoparasiticidal composition which overcomes or substantially mitigates the problems associated with flammability whilst at the same time providing an ectoparasiticidal composition which can be rinsed off hair and skin after use with conventional shampoo and conditioners.

The terms "flammable liquid" and "combustible liquid" are often used loosely to mean liquids which readily catch fire. However, herein the terms "flammable" and "combustible" are to be understood using the precise definitions applied to them by the National Fire Protection Association (NFPA) which is an internationally recognized US body concerned with fire safety. These definitions are also used by US Government agencies, in particular The US Department of Transportation, the US Environmental Protection Agency, the US Occupational Safety and Health Administration and others. These bodies apply the term "flammable" to a liquid which has a flash point below 100° F. (37.8° C.) and the term "combustible" to less-flammable liquids which have a flash point between 100° F. (37.8° C.) and 200° F. (93.3° C.). The flash point of a liquid is the lowest temperature at which it can form an ignitable mixture in air. At this temperature the vapour may cease to burn when the source of ignition is removed. A slightly higher temperature, the fire point, is defined as the temperature at which the vapour continues to burn after being ignited. Neither of these parameters is related to the temperature of the ignition source or of the burning liquid, which are much higher.

There are two basic types of flash point measurement: open cup and closed cup. Closed cup tests normally give lower values for the flash point than open cup tests and are a better approximation to the temperature at which the vapour pressure reaches a lower flammable limit. Accordingly, herein and in the appended claims the term flash point should be understood as that obtained using a Pensky-Martens closed cup method for which there are numerous international standards.

Surprisingly, the applicant has found that the use of a non-volatile low viscosity siloxane will act to spread a non-volatile high viscosity siloxane and that evaporation of the low viscosity siloxane is not required for the efficacy of the product.

Thus, according to a first aspect of the present invention there is provided an ectoparasiticidal composition comprising a mixture of a carrier and an active with an emulsifying agent, the carrier comprising a non-volatile low viscosity siloxane and the active comprising a non-volatile high viscosity siloxane, both the low viscosity siloxane and the high viscosity siloxane having a closed cup flash point of at least 100° C.

A flash point of at least 100° C. means that the siloxane in question will not form an ignitable mixture in air in normal usage of the composition.

Siloxanes may be either linear or cyclic siloxanes. Non-volatile siloxanes are usually linear. Preferably, the low viscosity siloxane and the high viscosity siloxane comprise a dimeticone or a dimeticonol or a mixture of same.

Dimeticones are linear siloxanes of the general formula $(C_2H_6OSi)_n$. They are otherwise known as polydimethylsiloxane (PDMS) and have previously been called 'dimethicone'. They are viscoelastic and their viscosity is related to their molecular weight.

Preferably also, the low viscosity siloxane has a viscosity in the range of 10 to 1000 centistokes inclusive and the high viscosity siloxane has a viscosity of at least 1000 centistokes. Advantageously, the low viscosity siloxane has a viscosity in the range of 10 to 100 centistokes inclusive and the high viscosity siloxane has a viscosity in the range of 50,000 to 200,000 centistokes inclusive.

Dimeticones with a viscosity of 10 centistokes are available that have a closed cup flash point of around 211° C. Dimeticones with viscosities less than 10 centistokes that have a closed cup flash point of greater than 200° C. are not currently commerically available. Dimeticones with viscosities in excess of 50,000 centistokes may have closed cup flash points in excess of 300° C. The use of these dimeticones in a composition according to the invention means that the composition does not comprise a flammable or combustible liquid and it does not, therefore, pose a fire hazard to the user. In particular, the composition is highly unlikely to enable a self-sustaining fire to arise on the hair or body in use if brought near to a naked flame. This makes the composition of the invention considerably safer to use than much of the prior art and makes it especially safe for use on children and infants.

The composition preferably comprises at least 0.1% of the non-volatile high viscosity siloxane and may comprise up to 50% but the actual proportion used will depend on its viscosity. Preferably, the composition itself has a viscosity in excess of 30 centistokes so that it adheres to the ectoparasites and their ova. Generally speaking, the higher the viscosity of the high viscosity siloxane used, the lower the proportion by volume required in the composition otherwise the composition is too viscous to use satisfactorily. In a composition comprising a high viscosity siloxane with a viscosity in the range of 50,000 to 200,000 centistokes inclusive, then only around 4% by volume of the composition need be the high viscosity siloxane.

In some formulations of the invention a viscosity modifier can be added to the basic composition to aid adhesion to the ectoparasites and their ova. Such a viscosity modifier preferably comprises a thixotropic additive to thicken the composition when in use. It may also stabilize the composition if any physically incompatible materials are added, for example hydrophobic silicone derivatives. Suitable viscosity modifiers will be known to those skilled in the art. One such is an additive in the form of silicon dioxide nano-size particles of between 7 nm and 40 nm in size. Preferably, the composition comprises at least 0.1% and up to 0.5% by volume of the additive.

In some prior art compositions, spreading agents are used to assist in the spreadability of the composition over skin and hair. These spreading agents reduce the surface tension of the composition. However, in the present invention no spreading agent is required as siloxanes can be used which have a surface tension that obviates their use. Advantageously, therefore, the siloxanes of the composition have a surface tension of the order of than 20 mN/m.

Preferably also, the emulsifying agent comprises a silicone copolymer. Advantageously, the composition comprises at least 1% and preferably between 1% and 10% by volume of an emulsifying agent comprising a dimeticone copolymer, for example a 40% solution of a dimeticone copolymer dispersed in cyclopentasiloxane. Such agents are readily commercially available and will be known to those skilled in the art as they are widely used in personal care products such as antiperspirants, cosmetics, shampoos and hair conditioners. They act as a stabilizing water-in-oil emulsifier and provide the rinse-off qualities required to make a composition in accordance with the invention wash off skin and hair easily and therefore make it more pleasant to use. While the emulsifying agent itself may have a flash point less than 200° C., the small quantity of emulsifying agent required in the composition does not compromise its overall flammability.

While mixtures of siloxanes are extremely effective in killing lice and fleas, their ova are more difficult to kill and may survive to cause reinfection after treatment. Preferably, therefore, the composition is modified to improve its efficacy as regards ova. Such a composition would have the considerable advantage that the number of treatments required for eradication of a louse infestation could be significantly reduced, in particular in the most effective compositions to a single treatment.

The applicant has found that by adding a terpene or a phenylpropanoid derivative to siloxane compositions, whilst having no inherent insecticidal properties, the surfactant physicochemical properties of the composition are improved and that a degree of hydrophillicity is added to the overall composition. This improves the penetrating properties of the composition and permits the high viscosity siloxane to penetrate the aeropyles of the ova in addition to the spiracles of the insects, thereby improving the overall effectiveness of the composition as a whole.

Preferably, therefore, the composition comprises an essential oil or essential oils. Preferably also, the composition comprises at least 0.1% by volume of the essential oil and may comprise up to 2% by volume of the essential oil. Advantageously, the essential oil or oils comprises one or more terpenes, in particular the essential oil comprises nerolidol.

In a second aspect the present invention provides the use of a composition in a method of treatment or prophylaxis of a human or animal wherein the composition a mixture of a carrier and an active with an emulsifying agent, the carrier comprising a non-volatile low viscosity siloxane and the active comprising a non-volatile high viscosity siloxane, both the low viscosity siloxane and the high viscosity siloxane having a closed cup flash point of at least 100° C.

In a third aspect the present invention provides a method of controlling an ectoparasitical infestation which comprises applying to said ectoparasite or its ovum a composition a mixture of a carrier and an active with an emulsifying agent, the carrier comprising a non-volatile low viscosity siloxane and the active comprising a non-volatile high viscosity siloxane, both the low viscosity siloxane and the high viscosity siloxane having a closed cup flash point of at least 100° C.

Two examples of formulations of an ectoparasiticidal composition in accordance with the invention are as follows.

EXAMPLE 1

1. 4% by volume of a dimeticone having a viscosity of 50,000 centistokes;
2. between 1% and 4% by volume of an emulsifying agent comprising a dimeticone copolymer;
3. up to 2% by volume of nerolidol;
4. a balance of a dimeticone having a viscosity of between 10 an 100 centistokes.

EXAMPLE 2

1. 4% by volume of a dimeticone having a viscosity of 100,000 centistokes;
2. between 1% and 4% by volume of an emulsifying agent comprising a dimeticone copolymer;
3. up to 2% by volume of nerolidol;
4. up to 0.5% by volume of silicon dioxide nano-size particles; and
5. a balance of a dimeticone having a viscosity of between 10 and 100 centistokes.

In particular, ectoparasiticidal compositions in accordance with the present invention have been developed for the convenience of particular users as liquid gel formulations for application by pouring on to the hair and as spray gel formulations for spraying onto the hair via a pump-action spray gun.

Specific examples of these formulations are as follows.

Liquid Gel Formulation
1. 4% by volume of a dimeticone having a viscosity of 100,000 centistokes;
2. 2% by volume of a dimeticone copolymer;
3. 2% by volume of nerolidol;
4. 0.5% by volume of silicon dioxide nano-size particles; and
5. 91.5% balance of dimeticone having a viscosity of 50 centistokes.

Spray Gel Formulation
1. 4% by volume of a dimeticone having a viscosity of 100,000 centistokes;
2. 2% by volume of a dimeticone copolymer;
3. 2% by volume of nerolidol;
4. 0.5% by volume of silicon dioxide nano-size particles; and
5. 91.5% balance of dimeticone having a viscosity of 10 centistokes.

It will be appreciated that the only difference between these formulations is the viscosity of the dimeticone carrier, which in the spray gel formulation has a lower viscosity for ease of application via a pump action spray gun.

In use for the treatment of head lice, the composition should be applied to dry hair and the hair should be fully covered from roots to tip. The composition should then be left in place for at least one hour.

Both of the examples were found to be a highly effective treatment of head lice and exhibit 100% lice kill typically within a few seconds of contact and 100% egg kill after one hour. After one hour the composition can be readily washed out with shampoo. The dead lice are washed out at the same time and can also be combed out easily. Any dead ova or nits, which are the empty egg cases, can also be removed by fingers or a fine-toothed comb. The treatment of other ectoparasites, such as fleas in animals, can be carried out in the same way.

The following tests illustrate the invention.

Test 1

This test compared the efficacy against head lice of a conventional siloxane based product as described in EP1215965 and comprising a mixture of 96.7% cyclopentasiloxane w/w and 3.3% dimethiconol w/w having a viscosity less than 20,000 centistokes (Formulation A) and of the spray gel formulation detailed above (Formulation B)

Materials and Methods

Insects Used in the Tests

Head lice, *Pediculus capitis*, were obtained from volunteers from the community. As a result lice used in the tests were obtained from different sources. On each day of testing all of the samples were evaluated once. For each of the tests performed on the same day all of the lice were obtained from the same individual patient so there was an internal consistency within a batch of test replicates. As only one replicate test of each formulation was performed on any one day there could have been some variation between tests conducted on different days. However, this would have represented the normal variation of head lice likely to be encountered in the community and any variation of response would be representative of the range of response likely to be encountered in consumer use.

Lice are collected using plastic louse detection combs and transported to the laboratory within 2 hours. Lice are counted into batches that are provided with squares of nylon gauze, as a substrate upon which to stand, and each batch allocated to a marked 55 millimeter plastic Petri dish.

For the test procedure an aliquot of approximately 5-10 milliliters of the appropriate formulation is poured into the base of a clean 55 millimeter plastic Petri dish. The gauze bearing the lice is immersed in the fluid for 10 seconds, during which time the gauze is turned at least twice to ensure removal of air bubbles. After removal from the fluid the gauze and insects are lightly blotted to remove excess fluid and returned to a 5.5 mm filter paper in their marked Petri dish. The same procedure is repeated for the other replicate gauze squares in that batch.

Gauze squares bearing the lice are then incubated under normal maintenance conditions (30°±2° Celsius and 50%±15% relative humidity) for the remainder of the test period. At the end of exposure period the insects and gauze are washed using a bland toiletry shampoo diluted one part shampoo with fourteen parts water (FWS 1:15) after which they are rinsed using 500 milliliters of warm (35° Celsius) tap water poured through and over the gauze squares. They are then blotted dry using medical wipe tissue and incubated under normal maintenance conditions in clean plastic Petri dishes of the appropriate size until the results are recorded.

Results

Activity Against Adult Lice

"Immobile" lice showing no signs of movement.

"Moribund" describes lice that retain some movement at the time the results are scored. Such movements can range from complete physical immobility, with just small movements of the gut observable, through minor twitches of limbs, antennae or other appendages, to insects that are nearly able to crawl but are sufficiently lacking in coordination that they could not be considered as capable of continued survival. Lice in this category are also classified in the overall mortality as being no longer effectively alive.

"Alive" describes lice that appear to walk normally and would be expected, given the opportunity to feed, to be able to continue life in a normal manner.

The tests were performed using one replicate lice for the test formulations and one replicate for the control. The tests were conducted ex vivo, with an application time of 1 hour, for all of the formulations and the control. The aim of these tests was to demonstrate the efficacy of the three products tested against lice from the field.

The results of the tests are shown in Table 1 below. The efficacy of the formulations is shown after a ten second dip and then an immediate wash off and a further set of tests is shown with a ten minute application and then wash off. These tests are to show whether either of the formulations has an immediate effect on the lice, and whether a ten minute application is successful at immobilising the lice.

TABLE 1

Results 1 hour after washing off

| Formulation | Exposure | Immobile | Morbid | Alive | Total | Mortality % |
|---|---|---|---|---|---|---|
| A | 10 minutes | 14 | 0 | 0 | 14 | 100% |
| B | 10 minutes | 13 | 0 | 0 | 13 | 100% |
| A | 10 second dip/wash off | 5 | 0 | 0 | 5 | 100% |
| B | 10 second dip/wash off | 5 | 0 | 0 | 5 | 100% |
| Control | 1 hour | 0 | 0 | 15 | 15 | 0% |

Results 2 hours after washing off

| Formulation | Exposure | Immobile | Morbid | Alive | Total | Mortality % |
|---|---|---|---|---|---|---|
| A | 10 minutes | 14 | 0 | 0 | 14 | 100% |
| B | 10 minutes | 13 | 0 | 0 | 13 | 100% |
| A | 10 second dip/wash off | 5 | 0 | 0 | 5 | 100% |
| B | 10 second dip/wash off | 5 | 0 | 0 | 5 | 100% |
| Control | 1 hour | 0 | 0 | 15 | 15 | 0% |

Results 3 hours after washing off

| Formulation | Exposure | Immobile | Morbid | Alive | Total | Mortality % |
|---|---|---|---|---|---|---|
| A | 10 minutes | 14 | 0 | 0 | 14 | 100% |
| B | 10 minutes | 13 | 0 | 0 | 13 | 100% |
| A | 10 second dip/wash off | 5 | 0 | 0 | 5 | 100% |
| B | 10 second dip/wash off | 5 | 0 | 0 | 5 | 100% |
| Control | 1 hour | 1 | 0 | 14 | 15 | 0% |

Results 17 hours after washing off

| Formulation | Exposure | Dead | Morbid | Alive | Total | Mortality % |
|---|---|---|---|---|---|---|
| B | 10 minutes | 13 | 0 | 0 | 13 | 100% |
| A | 10 second dip/wash off | 5 | 0 | 0 | 5 | 100% |
| B | 10 second dip/wash off | 5 | 0 | 0 | 5 | 100% |
| Control | 1 hour | 3 | 0 | 12 | 15 | 20% |

These test results show that a composition in accordance with the present invention is successful at instantly immobilizing lice after both exposure times.

Test 2

This test compared the efficacy against head lice ova of the liquid gel formulation and the spray gel formulation, both as detailed above, at two different exposure times. The two formulations were tested with exposure times of 15 minutes and 30 minutes Materials and Method Insects Used in the Tests Louse eggs were obtained by providing actively laying adults with a close meshed nylon gauze as an egg laying substrate over a 48 hour period. After removal of the lice each large gauze piece was cut into a series of smaller pieces of appropriate size and bearing a suitable number of eggs. These squares were allocated on a random basis to marked 90 millimeter plastic Petri dishes.

For the test an aliquot of approximately 5 milliliters of the appropriate fluid was poured into the base of a clean 30 millimeter plastic Petri dish. The gauze bearing the eggs was immersed in the liquid for 10 seconds, during which time the gauze was turned at least twice to ensure removal of air bubbles. After removal from the fluid the gauze and eggs were lightly blotted to remove any excess and returned to their marked Petri dish. The same procedure was repeated for the other test products and the water control.

Gauze squares bearing the eggs were incubated under normal maintenance conditions (30°±2° Celsius and 50%±15% relative humidity) for the remainder of the test period, at the end of which the gauze was rinsed three times using 250 milliliters of warm (34° Celsius) tap water poured through and over the gauze squares. They were then blotted dry using medical wipe tissue and incubated under normal maintenance conditions in clean plastic Petri dishes of the appropriate size until the results were recorded. The results of tests against eggs were recorded after all the control batch had completed hatching, approximately 12 days later.

Results

Activity Against Eggs

The activity of treatments against louse eggs requires classification of the effect according to the degree of penetration of the insecticide.

"Hatched" describes louse eggs in which the embryo inside develops normally and hatches normally.

"Half-hatched" describes those eggs in which the louse dies during the process of emergence so that it may only manage to lift the eggshell, or else dies partially emerged from the shell.

"Dead" Describes those eggs in which the embryo has apparently completed its development but which has not emerged from the eggshell. The young louse dies or is killed before or during the emergence process but before it is capable of lifting the lid from the eggshell.

"Undeveloped" is a description that is applied to all those eggs that fail to develop correctly or at all. This can be identified because at the time of testing the young embryos appear amorphous inside the transparent eggshell. When the developing embryo is about 48 hours old it starts to develop a small pigmented spot at the cap end of the shell. This spot will develop to become the eye of the louse and is referred to as the "eyespot". In some cases the embryo may develop only to the point of showing an eyespot but in these cases the spot is misshapen or may even be at the wrong end of the eggshell. All such cases are classified as "Undeveloped".

The results of the tests are shown in Table 2.

TABLE 2

| Formulation | Exposure Time | Total eggs | Hatched | Half-hatched | Killed | Under-developed | Mortality |
| --- | --- | --- | --- | --- | --- | --- | --- |
| Liquid Gel | 30 Minutes | 153 | 0 | 0 | 1 | 152 | 100% |
| Spray Gel | 30 Minutes | 177 | 0 | 0 | 0 | 177 | 100% |
| Liquid Gel | 15 Minutes | 130 | 0 | 0 | 14 | 116 | 100% |
| Spray Gel | 15 Minutes | 136 | 0 | 0 | 0 | 136 | 100% |

These results clearly demonstrate the efficacy of both formulations against louse ova at the different exposure times. Both produced 100% mortality with the 15 and 30 minute exposure times.

It will be seen from the test data above that the aforementioned liquid gel and spray gel formulations have been found to exhibit 100% lice kill on contact, typically within ten to fifteen seconds, and 100% egg kill after as little as fifteen minutes. This is a dramatic improvement over known formulations using siloxanes. WO2007/104345 discloses a composition comprising a mixture of a volatile dimeticone having a viscosity less than 10 centistokes and a dimeticone having a viscosity greater than 90 centistokes. However, using the same regime as indicated above in Test 2 this composition produces 82% egg kill for a one hour contact time. In WO2010/018,360 a siloxane formulation containing nerolidol is disclosed that has a most effective exposure time for egg kill of overnight although a four hour exposure period produced high levels of mortality at 92.85% compared to the overnight exposure which was 94.97%. Typically, therefore, the advice given to users of such formulations is to carry out two 1 hour treatments, seven days apart. However, the superior nature of the present invention is such that a cure can be achieved after a single 1 hour treatment. Indeed, the test data points to an efficacious treatment time of only around fifteen minutes being required.

Human head lice have a unique strategy of water management. They do not produce urine, but eliminate excess water by respiratory transpiration via the trachea and spiracles. Blockage of the spiracles prevents or reduces water excretion often leading to death by gut rupture.

Lice treated with the liquid gel formulation detailed above were scanned in a scanning electron microscope by x-ray spectroscopy and the chemical elements found in and around the spiracles of the lice were determined by cutting the surrounding tissues away using a focused ion beam and x-ray microanalysis. The results are shown in the attached drawings in which FIG. 1 is a photograph of an image produced by a scanning electron microscope of a spiracle of a human head louse after treatment with the liquid gel formulation detailed above;

Figure 1:
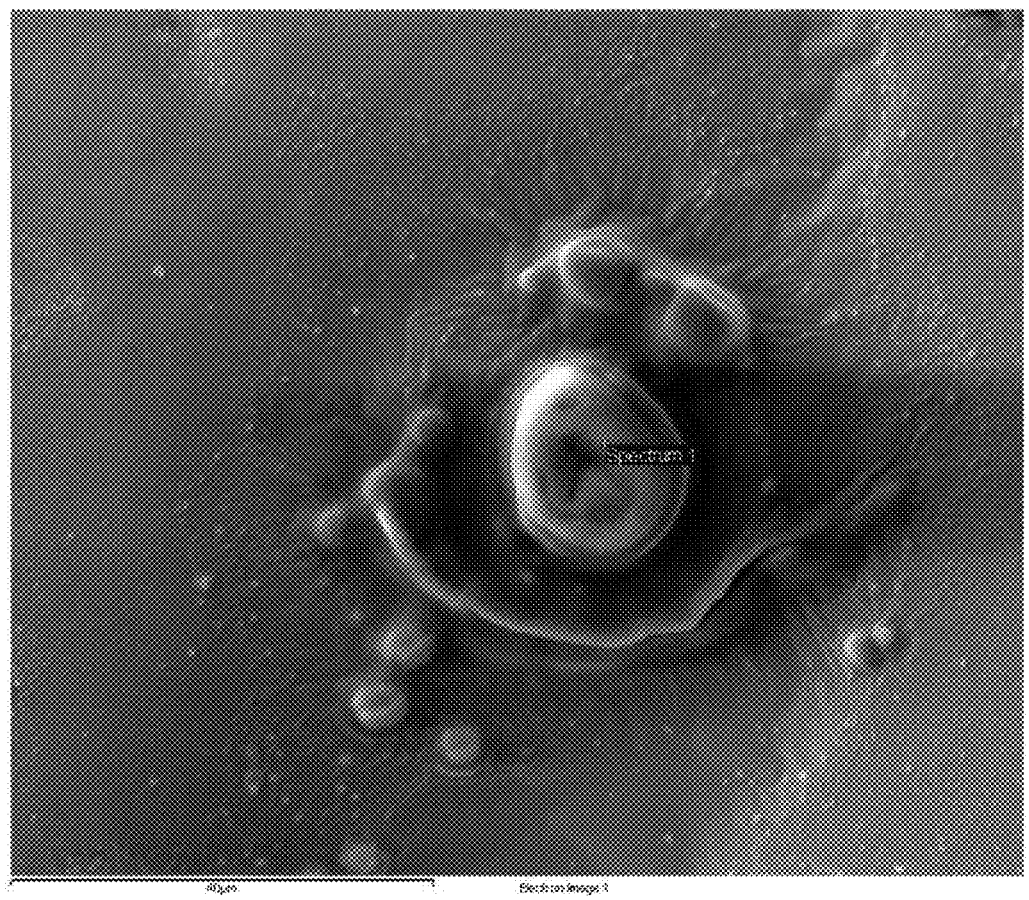
Figure 2:
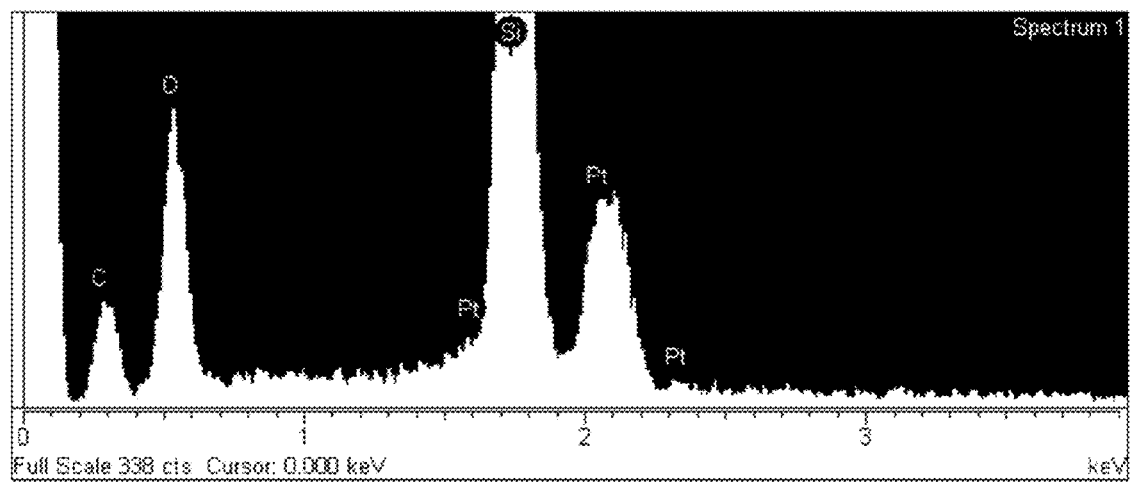
FIG. 2 is an x-ray spectrogram of the marked area in FIG. 1.
Figure 3:
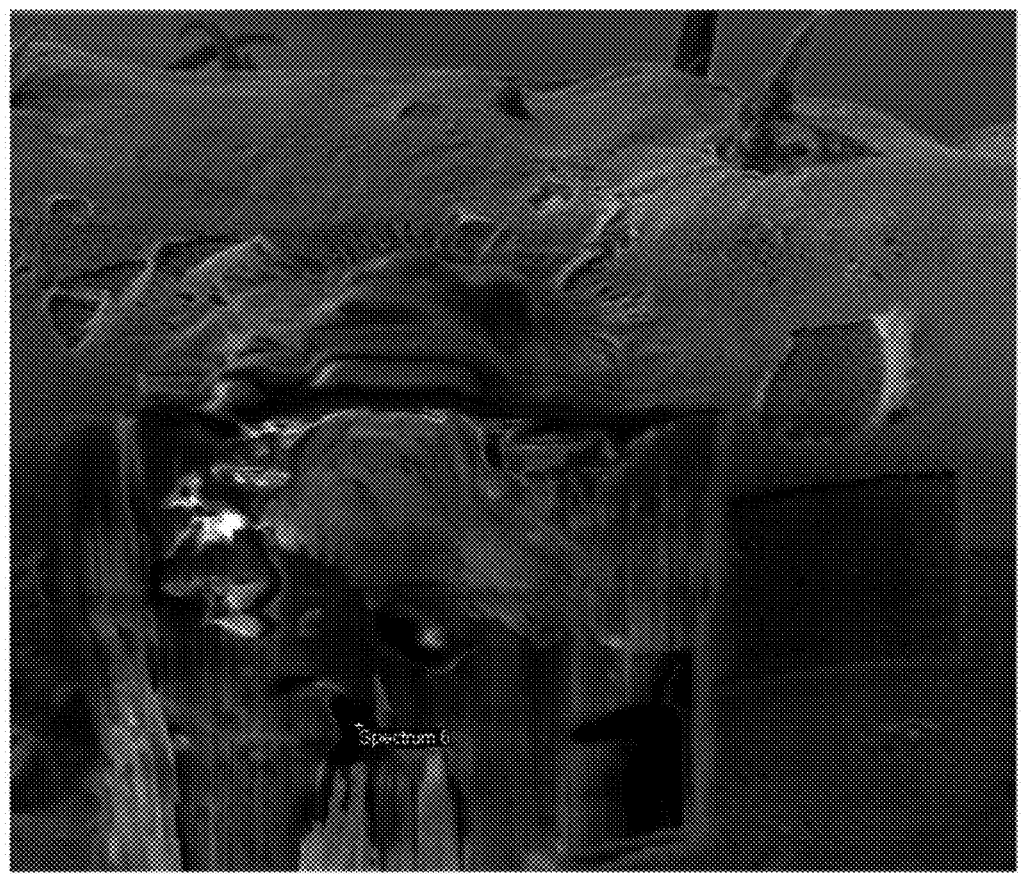
FIG. 3 is a photograph of an image produced by a scanning electron microscope of a cross-section through a spiracle of a human head louse after treatment with the liquid gel formulation detailed above.
Figure 4:
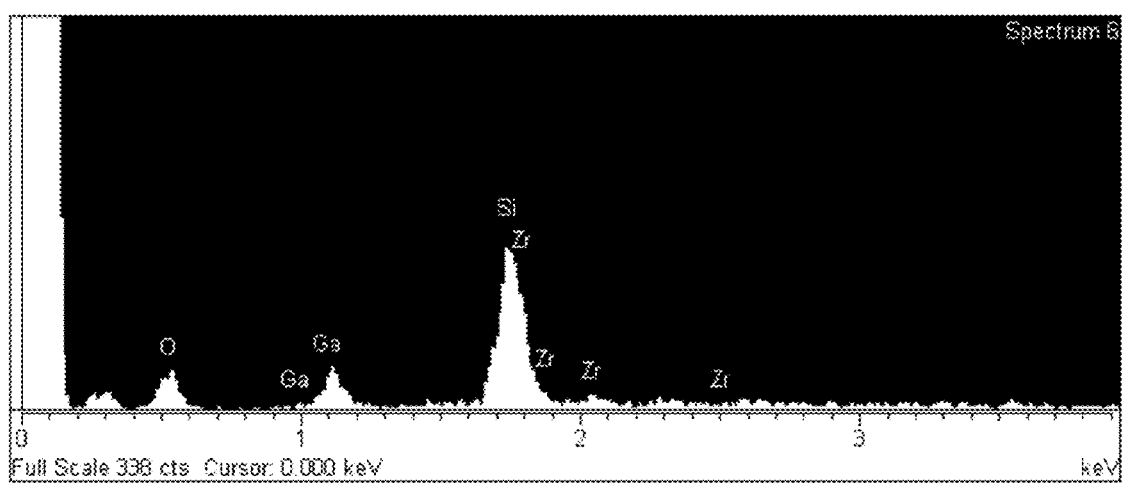
FIG. 4 is an x-ray spectrogram of the marked area in FIG. 3.

X-ray analysis showed silicone present over the whole surface of a treated louse; silicone being present in dimeticone but not in lice. As shown in FIG. 1, the silicone had formed a plug or a thin coating on the inside of the spiracles of treated lice. Ion beam cutting in the scanning electron microscope created a cross section of an abdominal spiracle as shown in FIG. 3. X-ray spectral analysis as shown in FIGS. 2 and 4 of the marked areas in FIGS. 1 and 3 respectively highlights the distribution of silicon from the dimeticone.

It is known that ectoparasiticidal formulations containing siloxanes work by blocking the spiracles of the louse thereby preventing water loss. Compositions in accordance with the invention work by the same mechanism. However, the images and spectrograms attached hereto show that significantly more silicone is deposited and left in the spiracles and on the surface of the lice (post washing) than with conventional compositions. In FIG. 1 a thick coating on the surface of the louse can be seen with a physical plug blocking the spiracle. FIG. 2 reveals the plug to be primarily silicone. Such a plug covering the spiracle can only be achieved by the non-volatile siloxanes used in the present formulations as they are sufficiently adhesive to the cuticle of the louse. Similarly, FIG. 3 showing the cross-section through a spiracle reveals penetration of the composition into the spiracle as far down as the trachea. FIG. 4 reveals a significant quantity of silicone present within the spiracle. These images and spectrograms explain the superior performance of compositions in accordance with the invention. In contrast, conventional siloxane compositions rely on very low viscosity, very low surface tension siloxane formulations that spread out thinly over the louse cuticle.

As regards the killing of head lice ova, as disclosed in WO2010/018360 it is thought that terpenoids and phenylpropanoid derivatives, and in particular linear terpenoids such as nerolidol, improve the penetrating characteristics of siloxanes into the aeropyles of the louse ovum. Lice eggs require oxygen/carbon dioxide gaseous exchange through their aeropyle openings in order to develop. Blocking this structure will prevent the egg from developing. The test results detailed above show that the liquid gel and spray formulations, which both contain nerolidol, are highly efficient at killing lice ova. While it is expected that nerolidol will improve the penetration of the siloxanes of compositions in accordance with the present invention into the aeropyles of the ova, it is also thought that the non-volatile siloxanes used in these compositions form plugs over the aeropyles in the same way as over the spiracles, effectively blocking them without necessarily needing to penetrate deeply into the aeropyle. This explains why the ova are killed very quickly.

The invention claimed is:

1. An ectoparasiticidal composition comprising a mixture of a carrier and an active with an emulsifying agent, the carrier comprising a nonvolatile low viscosity siloxane having a viscosity in the range of 10 to 1000 centistokes inclusive at 25° C. and the active comprising a nonvolatile high viscosity siloxane having a viscosity of at least 1000 centistokes at 25° C., both the low viscosity siloxane and the high viscosity siloxane having a closed cup flash point of at least 100° C.

2. The composition of claim 1, wherein both the low viscosity siloxane and the high viscosity siloxane comprise a dimeticone or a dimeticonol or a mixture of same.

3. The composition of claim 1, wherein the mixture has a viscosity in excess of 30 centistokes at 25 C.

4. The composition of claim 1, wherein both said the low viscosity siloxane and said the high viscosity siloxane have a surface tension of the order of 20 mN movable.

5. The composition of claim 1, wherein said the emulsifying agent comprises a silicone copolymer.

6. The composition of claim 5, comprising at least 1% by volume of the silicone copolymer.

7. The composition of claim 5, comprising between 1% and 10% by volume of the silicone copolymer.

8. The composition of claim 1, wherein said emulsifying agent comprises a 40% solution of a dimeticone copolymer dispersed in cyclopentasiloxane.

9. The composition of claim 1, wherein said low viscosity siloxane has a viscosity in the range of 10 to 100 centistokes inclusive at 25 C.

10. The composition of claim 1, wherein said high viscosity siloxane has a viscosity in the range of 50,000 to 200,000 centistokes at 25° C. inclusive.

11. The composition of claim 1, wherein said high viscosity siloxane comprises at least 0.1% by volume of the composition.

12. The composition of claim 1, further comprising an essential oil or essential oils.

13. The composition of claim 12, wherein the essential oil or oils comprise one or more terpenes.

14. The composition of claim 12, wherein the essential oil comprises nerolidol.

15. The composition of claim 12, wherein the essential oil or essential oils comprise at least 0.1% by volume of the composition.

16. The composition of claim 12, wherein the essential oil or essential oils comprise up to 2% by volume of the composition.

17. The composition of claim 1, further comprising:
    4% by volume of a dimeticone having a viscosity of 100,000 centistokes at 25° C.;
    between 1% and 4% by volume of an emulsifying agent comprising a dimeticone copolymer;
    up to 2% by volume of nerolidol; and
    a balance of a dimeticone having a viscosity of between 10 and 100 centistokes at 25° C.

18. The composition of claim 17, further comprising a balance of a dimeticone having a viscosity of 50 centistokes at 25° C.

19. The composition of claim 17, further comprising a balance of a dimeticone having a viscosity of 10 centistokes at 25° C.

20. The composition of claim 1, further comprising a thixotropic additive to thicken the composition when in use.

21. The composition of claim 20, wherein the thixotropic additive comprises silicon dioxide nano-size particles and is at least 0.1% by volume of the composition.

22. A composition for use in the treatment or prophylaxis of a human or animal of an infestation by ectoparasites wherein the composition comprises a mixture of a carrier and an active with an emulsifying agent, the carrier comprising anon-volatile low viscosity siloxane having a viscosity in the range of 10 to 1000 centistokes inclusive at 25° C. and the active comprising a non-volatile high viscosity siloxane having a viscosity of at least 1000 centistokes at 25° C., both the low viscosity siloxane and the high viscosity siloxane having a closed cup flash point of at least 100 C.

23. The composition of claim 22 for use in the treatment or prophylaxis of a head lice infestation.

24. A method of controlling an ectoparasitical infestation which comprises applying to said ectoparasite or its ovum a composition as claimed in claim 1.

* * * * *

UNITED STATES PATENT AND TRADEMARK OFFICE
CERTIFICATE OF CORRECTION

PATENT NO. : 8,530,451 B2  
APPLICATION NO. : 13/266230  
DATED : September 10, 2013  
INVENTOR(S) : Cooper Page 1 of 1

It is certified that error appears in the above-identified patent and that said Letters Patent is hereby corrected as shown below:

In the Claims

Column 11, Claim 3, line 28: The text "25 C" should read "25°C"

Column 11, Claim 4, line 31: The text "20 mN movable" should read "20 mN/m"

Column 11, Claim 9, line 43: The text "25 C" should read "25°C"

Column 12, Claim 22, line 42: The text "100 C" should read "100°C"

Signed and Sealed this
Eighth Day of April, 2014

Michelle K. Lee
*Deputy Director of the United States Patent and Trademark Office*